United States Patent
Wernick et al.

(10) Patent No.: US 12,061,257 B2
(45) Date of Patent: Aug. 13, 2024

(54) METHODS TO MAINTAIN IMAGE QUALITY IN ULTRASOUND IMAGING AT REDUCED COST, SIZE, AND POWER

(71) Applicant: eXo Imaging, Inc., Redwood City, CA (US)

(72) Inventors: Miles Wernick, Evanston, IL (US); Sandeep Akkaraju, Wellesley, MA (US); Drake Guenther, Hillsborough, CA (US); Kutay Ustuner, Mountain View, CA (US); Yusuf Haque, Woodside, CA (US)

(73) Assignee: Exo Imaging, Inc., Santa Clara, CA (US)

( * ) Notice: Subject to any disclaimer, the term of this patent is extended or adjusted under 35 U.S.C. 154(b) by 0 days.

(21) Appl. No.: 17/272,901

(22) PCT Filed: Dec. 20, 2019

(86) PCT No.: PCT/US2019/068004
§ 371 (c)(1),
(2) Date: Mar. 2, 2021

(87) PCT Pub. No.: WO2020/139775
PCT Pub. Date: Jul. 2, 2020

(65) Prior Publication Data
US 2021/0307726 A1    Oct. 7, 2021

Related U.S. Application Data

(60) Provisional application No. 62/785,315, filed on Dec. 27, 2018.

(51) Int. Cl.
*A61B 8/08*    (2006.01)
*G01S 7/52*    (2006.01)
*G01S 15/89*   (2006.01)

(52) U.S. Cl.
CPC ...... *G01S 15/8977* (2013.01); *G01S 7/52077* (2013.01); *G01S 7/52085* (2013.01); *G01S 7/52096* (2013.01); *G01S 15/8979* (2013.01)

(58) Field of Classification Search
CPC ....... A61B 8/483; A61B 8/488; A61B 8/5215; A61B 8/5238; A61B 8/5246; A61B 8/54;
(Continued)

(56) References Cited

U.S. PATENT DOCUMENTS 4,211,949 A    7/1980 Brisken et al.
4,281,298 A    7/1981 Gounji et al.
(Continued)

FOREIGN PATENT DOCUMENTS

JP    2015129987 A    7/2015
JP      6236731 B1    11/2017
(Continued)

OTHER PUBLICATIONS

O'Donnell, M. et al., "Phase-Aberration Correction Using Signals From Point Reflectors and Diffuse Scatterers: Measurements," IEEE Transactions on Ultrasonics, Ferroelectrics and Frequency Control, vol. 35, Issue 6, Nov. 1988, IEEE, pp. 768-774. (Year: 1988).*

(Continued)

*Primary Examiner* — Alexei Bykhovski
(74) *Attorney, Agent, or Firm* — Morgan, Lewis & Bockius LLP

(57) ABSTRACT

Disclosed herein are computer-implemented medical ultrasound imaging methods, and systems for performing the methods, that comprise forming a first frame of an ultrasound image sequence with high image quality; forming at least one frame of the ultrasound image sequence with reduced image quality; forming a second frame of the ultrasound image sequence with high image quality; and (Continued)

improving the quality of the at least one frame of the ultrasound image sequence with reduced image quality using the first and/or the second frames of the ultrasound image sequence with high quality. In some cases, the improvement of the quality of the at least one frame of the ultrasound image sequence with reduced image quality is achieved by application of machine learning.

48 Claims, 3 Drawing Sheets

(58) Field of Classification Search
CPC ........ A61B 8/5269; G06T 2207/10132; G06T 5/50; G06T 2207/10081; G06T 2207/10088; G06T 2207/10101; G06T 2207/20081; G06T 5/001; G01S 15/8977; G01S 7/52077; G01S 7/52085; G01S 7/52096; G01S 15/8979; G16H 30/40
See application file for complete search history.

(56) References Cited

U.S. PATENT DOCUMENTS

| | | | |
|---|---|---|---|
| 4,290,127 A * | 9/1981 | Pridham | H01Q 3/42 342/372 |
| 4,375,042 A | 2/1983 | Marcus | |
| 4,731,865 A | 3/1988 | Sievenpiper | |
| 5,520,187 A | 5/1996 | Snyder | |
| 5,605,154 A | 2/1997 | Ries et al. | |
| 5,969,621 A | 10/1999 | Getman et al. | |
| 6,023,977 A | 2/2000 | Langdon et al. | |
| 6,083,168 A | 7/2000 | Hossack et al. | |
| 6,108,121 A | 8/2000 | Mansell et al. | |
| 6,359,367 B1 | 3/2002 | Sumanaweera et al. | |
| 6,669,638 B1 * | 12/2003 | Miller | A61B 8/546 600/438 |
| 7,005,776 B1 | 2/2006 | Iino et al. | |
| 7,046,734 B2 * | 5/2006 | McVeigh | H04N 19/137 375/E7.15 |
| 7,532,093 B1 | 5/2009 | Pulskamp et al. | |
| 8,004,158 B2 | 8/2011 | Hielscher | |
| 10,605,903 B2 * | 3/2020 | von Ramm | B06B 1/0625 |
| 10,835,209 B2 | 11/2020 | Haque et al. | |
| 2001/0005776 A1 | 6/2001 | Holley et al. | |
| 2003/0178914 A1 | 9/2003 | Ogawa et al. | |
| 2003/0181814 A1 | 9/2003 | Ji et al. | |
| 2004/0195937 A1 | 10/2004 | Matsubara et al. | |
| 2005/0025377 A1 | 2/2005 | Avinash et al. | |
| 2005/0228282 A1 | 10/2005 | Wang et al. | |
| 2006/0113866 A1 | 6/2006 | Ganor | |
| 2006/0122486 A1 | 6/2006 | Tamez-Pena et al. | |
| 2006/0173313 A1 | 8/2006 | Liu et al. | |
| 2007/0167752 A1 | 7/2007 | Proulx et al. | |
| 2008/0087089 A1 | 4/2008 | Nam | |
| 2008/0255451 A1 | 10/2008 | Cohen et al. | |
| 2010/0020645 A1 | 1/2010 | Wodnicki et al. | |
| 2010/0168583 A1 | 7/2010 | Dausch et al. | |
| 2010/0266186 A1 | 10/2010 | Hebrank et al. | |
| 2011/0051461 A1 | 3/2011 | Buchwald et al. | |
| 2011/0249878 A1 | 10/2011 | Pagoulatos et al. | |
| 2012/0116220 A1 | 5/2012 | Burcher et al. | |
| 2012/0127136 A1 | 5/2012 | Schneider et al. | |
| 2012/0146642 A1 | 6/2012 | Du | |
| 2013/0303919 A1 | 11/2013 | Corl | |
| 2014/0024928 A1 | 1/2014 | Boctor et al. | |
| 2014/0117812 A1 | 5/2014 | Hajati | |
| 2014/0219063 A1 | 8/2014 | Hajati et al. | |
| 2014/0328504 A1 | 11/2014 | Stephanou et al. | |
| 2014/0355377 A1 | 12/2014 | Hiriyannaiah | |
| 2015/0023561 A1 | 1/2015 | Hamilton | |
| 2015/0080725 A1 * | 3/2015 | Wegner | G01S 15/8997 600/440 |
| 2015/0160322 A1 | 6/2015 | Matthews | |
| 2015/0201909 A1 * | 7/2015 | Yamamoto | G01S 7/52049 600/442 |
| 2015/0265245 A1 | 9/2015 | Von Ramm et al. | |
| 2015/0272547 A1 * | 10/2015 | Freiburger | A61B 8/52 600/438 |
| 2015/0333730 A1 | 11/2015 | Meltaus et al. | |
| 2016/0055627 A1 | 2/2016 | Shibata et al. | |
| 2016/0107194 A1 | 4/2016 | Panchawagh et al. | |
| 2016/0211828 A1 | 7/2016 | Simmonds et al. | |
| 2016/0262725 A1 | 9/2016 | Boser et al. | |
| 2016/0288168 A1 | 10/2016 | Hynynen et al. | |
| 2016/0331345 A1 | 11/2016 | Kong et al. | |
| 2017/0000461 A1 | 1/2017 | Wong et al. | |
| 2017/0224312 A1 | 8/2017 | Call et al. | |
| 2017/0262598 A1 | 9/2017 | Petkov et al. | |
| 2017/0328870 A1 | 11/2017 | Garlepp et al. | |
| 2017/0372193 A1 | 12/2017 | Mailhe et al. | |
| 2018/0153510 A1 | 6/2018 | Haque et al. | |
| 2018/0154393 A1 | 6/2018 | Viegas et al. | |
| 2018/0177461 A1 | 6/2018 | Bell et al. | |
| 2018/0192999 A1 | 7/2018 | Song et al. | |
| 2018/0293762 A1 | 10/2018 | Fu et al. | |
| 2018/0353157 A1 * | 12/2018 | Eibl | A61B 8/4281 |
| 2019/0184426 A1 | 6/2019 | Kojima et al. | |
| 2020/0175675 A1 * | 6/2020 | Ogino | A61B 6/03 |
| 2021/0022706 A1 | 1/2021 | Haque et al. | |
| 2021/0022707 A1 | 1/2021 | Haque et al. | |

FOREIGN PATENT DOCUMENTS

| | | |
|---|---|---|
| KR | 20080034660 A | 4/2008 |
| WO | WO-2013044471 A1 | 4/2013 |
| WO | WO-2013/110174 A1 | 8/2013 |
| WO | WO-2014/069558 A1 | 5/2014 |
| WO | WO-2018102621 A1 | 6/2018 |
| WO | WO-2018102622 A1 | 6/2018 |
| WO | WO-2020068473 A1 | 4/2020 |
| WO | WO-2020139775 A1 | 7/2020 |

OTHER PUBLICATIONS

APC International, Ceramic manufacturing series—poling PZT ceramics. https://www.americanpiezo.com/blog/ceramic-manufacturing-series-poling-pzt-ceramics/ [1-3] (2016).

Assef et al., A reconfigurable arbitrary waveform generator using PWM modulation for ultrasound research. BioMedical Engineering OnLine 12:24 [1-13] (2013).

Choudhry et al., Comparison of tissue harmonic imaging with conventional US in abdominal disease. RadioGraphics: Imaging and Therapeutic Technology 20:1127-1135 (2000).

Dahl, Ultrasound beamforming and image formation. http://people.duke.edu/-jjd/RSNA_USbeamforming.pdf [Slide presentation] (c. 2005).

Dausch et al., Theory and operation of 2-D array piezoelectric micromachined ultrasound transducers. IEEE Transactions on Ultrasonics, Ferroelectrics, and Frequency Control 55(11):2484-2492 (2008).

Doerry, Generating nonlinear FM chirp waveforms for radar. Sandia Report, SAND2006-5856:1-34 (2006).

Felix et al., Biplane ultrasound arrays with integrated multiplexing solution for enhanced diagnostic accuracy in endorectal and transvaginal imaging. http://www.vermon.com/vermon/publications/Felix_UFFC_2005.pdf (2005).

Goldman, Apple's Lightning connector and you: what you should know. CNET Sep. 19, 2012: https://www.cnet.com/news/apples-lightning-connector-and-you-what-you-should-know/ (2012).

Guedes et al., Aluminum nitride pMUT based on a flexurally-suspended membrane. IEEE 16th International Solid-State Sensors, Actuators and Microsystems Conference:12169346 (2011).

Hajati et al., Three-dimensional micro electromechanical system piezoelectric ultrasound transducer. Appl. Phys. Lett. 101:253101 (2012); doi: 10.1063/1.4772469 (2012).

Harput, Use of chirps in medical ultrasound imaging. Ultrasound Group, School of Electronic and Electrical Engineering, University Of Leeds, PHD Thesis, Dec. 2012.

(56) References Cited

OTHER PUBLICATIONS

Karki, Signal conditioning piezoelectric sensors. Texas Instruments Application report, SLA033A:1-5 (2000).

Khuri-Yakub et al., Capacitive micro machined ultrasonic transducers for medical imaging and therapy. Journal of Micromech Microeng. 21(5):054004-054014 (2011).

Lach et al., Piezoelectric materials for ultrasonic probes. http://www.ndt.net/article/platte2/platte2.htm NDTnet 1(9):1-9 (1996).

Lee et al., Wafer-to-wafer alignment for three-dimensional integration: a review. Journal of MicroElectroMechanical Systems 20(4):885-898 (2011).

Lu et al., High frequency piezoelectric micromachined ultrasonic transducer array for intravascular ultrasound imaging. Proceedings of the IEEE International Conference on Micro Electro Mechanical Systems (MEMS):06765748 (2014).

Martin, Introduction to B-mode imaging. Cambridge University Press; Diagnostic Ultrasound: Physics and equipment, 2nd Edition. Chapter 1:1-10 (2010).

Mina, High frequency transducers from PZT films. Materials Science and Engineering Thesis; Pennsylvania State University:1-199 (2007).

Moazzami et al., Electrical characteristics of ferroelectric PZT thin films for DRAM applications. IEEE Transaction on Electron Devices 39(9):2044-2049 (1992).

Orenstein Scanning in pain—sonographers seek relief from job-related hazard. Radiology Today 10(8):24 (2009).

Ovland, Coherent plane-wave compounding in medical ultrasound imaging. NTNU—Trondheim, Norwegian University of Science and Technology, Master of Science Thesis, 1-62 (Jun. 2012).

PCT/US2017/064090 International Search Report and Written Opinion dated Mar. 28, 2018.

PCT/US2017/064091 International Search Report and Written Opinion dated Mar. 28, 2018.

PCT/US2019/051238 International Search Report and Written Opinion dated Dec. 19, 2019.

PCT/US2019/068004 International Search Report and Written Opinion dated Apr. 21, 2020.

Pye et al., Adaptive time gain compensation for ultrasonic imaging. Ultrasound in Medicine and Biology 18(2):205-212 [abstract] (1992).

Rodriguez et al., Low cost matching network for ultrasonic transducers. Physics Procedia 3:1025-1031 (2010).

Smyth, Design and modeling of a PZT thin film based piezoelectric micromachined ultrasonic transducer (PMUT). MSME Thesis, MIT:1-156 (2012).

Spectral doppler. http://www.echocardiographer.org/Echo%20Physics/spectral%20doppler.html (2017).

Szabo. Diagnostic ultrasound imaging: inside out. Elsevier Academic Press, ISBN: 0-12-680145-2 (572 pgs) (2014).

Trots et al., Synthetic aperture method in ultrasound imaging. InTech Press; Ultrasound Imaging, Masayuki Tanabe (Ed.). http://www.intechopen.com/books/ultrasound-imaging/synthetic-aperture-method-in-ultrasound-imaging. Chapter 3:37-56 (2011).

U.S. Appl. No. 15/826,614 Office Action dated Oct. 1, 2020.

Wang et al., Broadband piezoelectric micromachined ultrasonic transducer (pMUT) using mode-merged design. Proceedings of the 10th IEEE International Conference on Nano/Micro Engineered and Molecular Systems (IEEE-NEMS 2015):15260900. Xi'an, China, Apr. 7-11, 2015.

Wang et al., Zero-bending piezoelectric micromachined ultrasonic transducer (pMUT) with enhanced transmitting performance. Journal of Microelectromechanical Systems 24(6):2083-2091 (2015).

\* cited by examiner

METHODS TO MAINTAIN IMAGE QUALITY IN ULTRASOUND IMAGING AT REDUCED COST, SIZE, AND POWER

CROSS-REFERENCE TO RELATED APPLICATIONS

This application is the National Stage entry of International Application No. PCT/US2019/068004, filed Dec. 20, 2019, which claims the benefit of U.S. Provisional Application No. 62/785,315, filed Dec. 27, 2018, both of which are herein incorporated by reference in their entireties.

BACKGROUND

Ultrasound imaging is widely used in the fields of medicine and non-destructive testing.

SUMMARY

Typical ultrasound imaging devices are bulky and costly, and there exists a need for small, portable, and low-cost devices. Portability of an ultrasound imaging device demands that its electrical power requirements be minimized.

Cost, size and power consumption of an ultrasound imaging device can be reduced through various modifications of the process by which the ultrasound pulses are produced and sensed. The modifications to reduce power consumption include reducing active channel count, front-end gain and bias, analog-to-digital conversion (ADC) sampling rate, lateral sampling rate, temporal sampling rate, number of parallel receive beams, beam-bandwidth product, filter kernel lengths, filter coefficient quantization levels, data rate and word length, ensemble length for Doppler, etc. However, such modifications generally result in reduced image quality in the form of a combination of reduced spatial resolution, contrast resolution, temporal resolution, sensitivity, penetration, and dynamic range, or increased imaging and spectral artifacts. There is a perceived risk that current methodologies may fail to accurately represent subtle image details that convey important diagnostic information.

There exists a need to counteract these reductions in image quality so that good image quality can be achieved with low cost, low performance, small form factor integrated circuits and processors at reduced levels of power consumption. Accordingly, the subject matter described herein, in some embodiments, uses machine learning to permit ultrasound images to be produced with lower cost, lower power and smaller form factor devices without the associated loss of image quality. In some embodiments, the subject matter described herein makes use of high-quality and reduced-quality frames. In further embodiments, the subject matter described herein makes alternating use of high-quality and reduced-quality frames. In so doing, the subject matter described herein, in such embodiments, incorporates high-quality images periodically during processing to minimize risk of failing to accurately represent subtle image details by ensuring that high-quality image details are available to the model.

In one aspect, disclosed herein are computer-implemented medical ultrasound imaging methods comprising: forming a first frame of an ultrasound image sequence with high image quality; forming at least one frame of the ultrasound image sequence with reduced image quality; forming a second frame of the ultrasound image sequence with high image quality; and improving the quality of the at least one frame of the ultrasound image sequence with reduced image quality using the first or the second frames of the ultrasound image sequence with high quality. In some embodiments, the quality of the at least one frame of the ultrasound image sequence with reduced image quality is improved by using the first and the second frame of the ultrasound image sequence with high quality. In some embodiments, the method further comprises improving the quality of the first frame of the ultrasound image sequence with high image quality or the second frame of the ultrasound image sequence with high image quality. In various embodiments, the image quality comprises spatial resolution, contrast resolution, signal-to-noise ratio, and/or signal dynamic range. In some embodiments, each frame is a 2-dimensional image. In other embodiments, each frame is a 3-dimensional image. In some embodiments, each frame is a B-Mode image. In other embodiments, each frame is a color Doppler image. In yet other embodiments, each frame is a spectral Doppler strip. In some embodiments, the improving the quality of the at least one frame of the ultrasound image sequence with reduced image quality is achieved by application of machine learning. In some embodiments, the reduced image quality is at least partially the result of low spatial sampling incurred by using a reduced number of transducer elements. In some embodiments, the reduced image quality is at least partially the result of low temporal sampling incurred by using a low temporal sampling rate. In some embodiments, the reduced image quality is at least partially the result of low spatial frequency sampling. In some embodiments, the reduced image quality is at least partially the result of temporal delay quantization used during the beamforming process. In some embodiments, the reduced image quality is at least partially due to not performing phase aberration correction. In some embodiments, the reduced image quality is at least partially due to not performing aperture coherence function-based imaging techniques. In some embodiments, the reduced image quality is at least partially due to a reduced number of transmissions (line spacing and ensemble length). In various embodiments, the reduced image quality is due to a combination of two or more techniques used to reduce image quality selected from the list consisting of: low spatial sampling incurred by using a reduced number of elements of the ultrasound transducer, low temporal sampling incurred by using a low temporal sampling rate, low spatial frequency sampling, temporal delay quantization used during a beamforming process, not performing phase aberration correction, not performing aperture coherence function-based imaging techniques, and sending a reduced number of transmissions (line spacing and ensemble length). In some embodiments, the frames are formed using a transducer, and wherein the transducer comprises a pMUT device. In some embodiments, the frames are formed using a transducer and the transducer comprises a 1.25D, 1.5D, 1.75D, or 2D array.

In another aspect, disclosed herein are medical ultrasound imaging systems comprising: a medical ultrasound imaging device comprising an ultrasound transducer; and at least one processor; the system configured to perform functions comprising: forming, using the ultrasound transducer, a first frame of an ultrasound image sequence with high image quality; forming, using the ultrasound transducer, at least one frame of the ultrasound image sequence with reduced image quality; forming, using the ultrasound transducer, a second frame of the ultrasound image sequence with high image quality; and improving, using the at least one processor, the quality of the at least one frame of the ultrasound image sequence with reduced image quality using the first or the second frames of the ultrasound image sequence with high quality. In some embodiments, the quality of the at least one frame of the ultrasound image sequence with reduced image quality is improved by using the first and the second frame of the ultrasound image sequence with high quality. In some embodiments, the system is further configured to perform functions comprising: improving the quality of the first frame of the ultrasound image sequence with high image quality or the second frame of the ultrasound image sequence with high image quality. In various embodiments, image quality comprises spatial resolution, contrast resolution, signal-to-noise ratio, and/or signal dynamic range. In some embodiments, each frame is a 2-dimensional image. In other embodiments, each frame is a 3-dimensional image. In some embodiments, each frame is a B-Mode image. In some embodiments, each frame is a color Doppler image. In some embodiments, each frame is a spectral Doppler strip. In some embodiments, the improving the quality of the at least one frame of the ultrasound image sequence with reduced image quality is achieved by application of machine learning. In some embodiments, the reduced image quality is the result of low spatial sampling incurred by using a reduced number of elements of the ultrasound transducer. In some embodiments, the reduced image quality is the result of low temporal sampling incurred by using a low temporal sampling rate. In some embodiments, the reduced image quality is the result of low spatial frequency sampling. In some embodiments, the reduced image quality is the result of temporal delay quantization used during a beamforming process. In some embodiments, the reduced image quality is due to not performing phase aberration correction. In some embodiments, the reduced image quality is due to not performing aperture coherence function-based imaging techniques. In some embodiments, the reduced image quality is due to a reduced number of transmissions (line spacing and ensemble length). In various embodiments, the reduced image quality is due to a combination of two or more techniques used to reduce image quality selected from the list consisting of: low spatial sampling incurred by using a reduced number of elements of the ultrasound transducer, low temporal sampling incurred by using a low temporal sampling rate, low spatial frequency sampling, temporal delay quantization used during a beamforming process, not performing phase aberration correction, not performing aperture coherence function-based imaging techniques, and sending a reduced number of transmissions (line spacing and ensemble length). In some embodiments, the ultrasound transducer comprises a pMUT device. In some embodiments, the ultrasound transducer comprises a 1.25D, 1.5D, 1.75D, or 2D array of elements. In some embodiments, the at least one processor comprises an application-specific integrated circuit (ASIC). In some embodiments, the at least one processor comprises a mobile computing device in communication with the medical ultrasound imaging device.

BRIEF DESCRIPTION OF THE DRAWINGS

A better understanding of the features and advantages of the present subject matter will be obtained by reference to the following detailed description that sets forth illustrative embodiments and the accompanying drawings of which.

DETAILED DESCRIPTION

Figure 1:
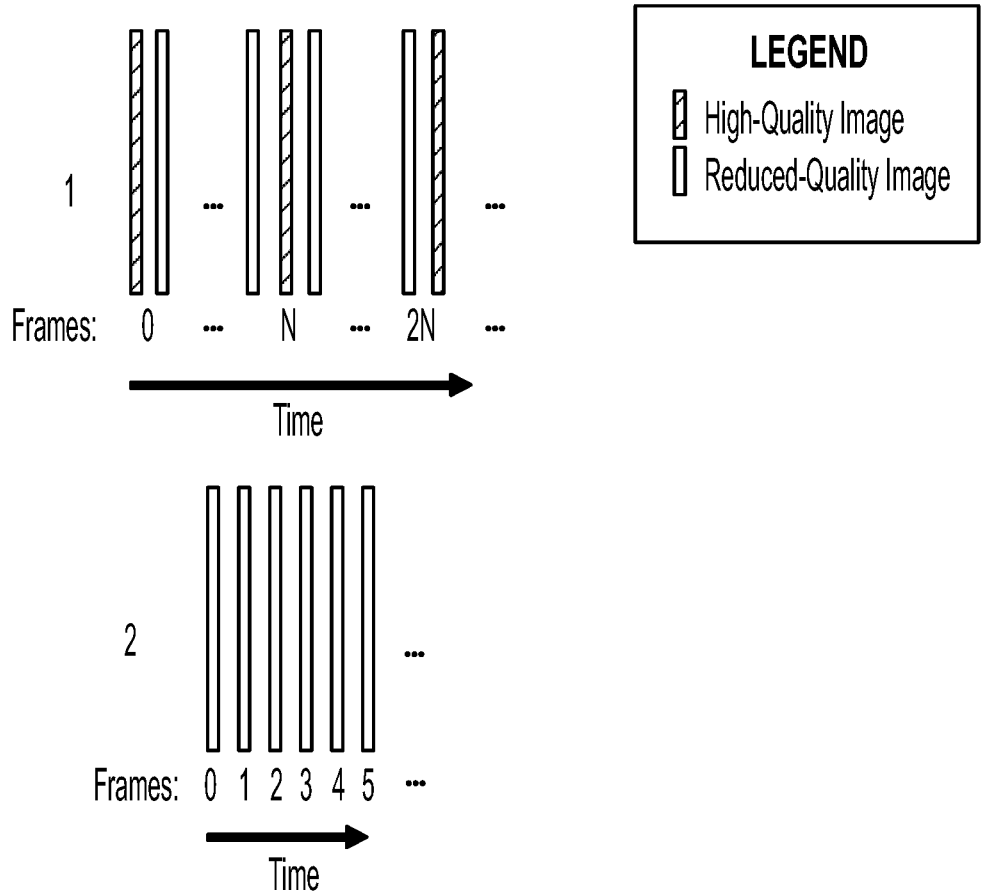
FIG. 1 illustrates two scan procedures: in Scan Procedure 1, every Nth frame is a High-Quality Image and all the other frames are Reduced-Quality Images; and in Scan Procedure 2, all the frames are Reduced-Quality Images.

Disclosed herein, in some embodiments, are computer-implemented medical ultrasound imaging methods comprising: forming a first frame of an ultrasound image sequence with high image quality; forming at least one frame of the ultrasound image sequence with reduced image quality; forming a second frame of the ultrasound image sequence with high image quality; and improving the quality of the at least one frame of the ultrasound image sequence with reduced image quality using the first or the second frames of the ultrasound image sequence with high quality. In some embodiments, the quality of the at least one frame of the ultrasound image sequence with reduced image quality is improved by using the first and the second frame of the ultrasound image sequence with high quality. In some embodiments, the method further comprises improving the quality of the first frame of the ultrasound image sequence with high image quality or the second frame of the ultrasound image sequence with high image quality. In some embodiments, the image quality comprises spatial resolution. In some embodiments, the image quality comprises contrast resolution. In some embodiments, the image quality comprises signal-to-noise ratio. In some embodiments, the image quality comprises signal dynamic range. In some embodiments, each frame is a 2-dimensional image. In other embodiments, each frame is a 3-dimensional image. In some embodiments, each frame is a B-Mode image. In other embodiments, each frame is a color Doppler image. In yet other embodiments, each frame is a spectral Doppler strip. In some embodiments, the improving the quality of the at least one frame of the ultrasound image sequence with reduced image quality is achieved by application of machine learning. In some embodiments, the reduced image quality is at least partially the result of low spatial sampling incurred by using a reduced number of transducer elements. In some embodiments, the reduced image quality is at least partially the result of low temporal sampling incurred by using a low temporal sampling rate. In some embodiments, the reduced image quality is at least partially the result of low spatial frequency sampling. In some embodiments, the reduced image quality is at least partially the result of temporal delay quantization used during the beamforming process. In some embodiments, the reduced image quality is at least partially due to not performing phase aberration correction. In some embodiments, the reduced image quality is at least partially due to not performing aperture coherence function-based imaging techniques. In some embodiments, the reduced image quality is at least partially due to a reduced number of transmissions (line spacing and ensemble length). In some embodiments, the reduced image quality is at least partially due to a combination of two or more of the above techniques used to reduce image quality. In some embodiments, the frames are formed using a transducer, and wherein the transducer used is a pMUT device. In some embodiments, the frames are formed using a transducer, and wherein the transducer used is a 1.25D, 1.5D, 1.75D, or 2D array.

Also, disclosed herein, in some embodiments, are medical ultrasound imaging systems comprising: a medical ultrasound imaging device comprising an ultrasound transducer; and at least one processor; the system configured to perform functions comprising: forming, using the ultrasound transducer, a first frame of an ultrasound image sequence with high image quality; forming, using the ultrasound transducer, at least one frame of the ultrasound image sequence with reduced image quality; forming, using the ultrasound transducer, a second frame of the ultrasound image sequence with high image quality; and improving, using the at least one processor, the quality of the at least one frame of the ultrasound image sequence with reduced image quality using the first or the second frames of the ultrasound image sequence with high quality. In some embodiments, the quality of the at least one frame of the ultrasound image sequence with reduced image quality is improved by using the first and the second frame of the ultrasound image sequence with high quality. In some embodiments, the device is further configured to perform functions comprising: improving the quality of the first frame of the ultrasound image sequence with high image quality or the second frame of the ultrasound image sequence with high image quality. In various embodiments, image quality comprises spatial resolution, contrast resolution, signal-to-noise ratio, and/or signal dynamic range. In some embodiments, each frame is a 2-dimensional image. In other embodiments, each frame is a 3-dimensional image. In some embodiments, each frame is a B-Mode image. In some embodiments, each frame is a color Doppler image. In some embodiments, each frame is a spectral Doppler strip. In some embodiments, the improving the quality of the at least one frame of the ultrasound image sequence with reduced image quality is achieved by application of machine learning. In some embodiments, the reduced image quality is the result of low spatial sampling incurred by using a reduced number of elements of the ultrasound transducer. In some embodiments, the reduced image quality is the result of low temporal sampling incurred by using a low temporal sampling rate. In some embodiments, the reduced image quality is the result of low spatial frequency sampling. In some embodiments, the reduced image quality is the result of temporal delay quantization used during a beamforming process. In some embodiments, the reduced image quality is due to not performing phase aberration correction. In some embodiments, the reduced image quality is due to not performing aperture coherence function-based imaging techniques. In some embodiments, the reduced image quality is due to a reduced number of transmissions (line spacing and ensemble length). In various embodiments, the reduced image quality is due to a combination of two or more techniques used to reduce image quality selected from the list consisting of: low spatial sampling incurred by using a reduced number of elements of the ultrasound transducer, low temporal sampling incurred by using a low temporal sampling rate, low spatial frequency sampling, temporal delay quantization used during a beamforming process, not performing phase aberration correction, not performing aperture coherence function-based imaging techniques, and sending a reduced number of transmissions (line spacing and ensemble length). In some embodiments, the ultrasound transducer comprises a pMUT device. In some embodiments, the ultrasound transducer comprises a 1.25D, 1.5D, 1.75D, or 2D array of elements. In some embodiments, the at least one processor comprises an application-specific integrated circuit (ASIC).

Machine Learning Terms

A machine learning algorithm ("Model") is a mathematical function $f(x; w)$ in which x ("Input") is a vector (list) of mathematical variables, y ("Label") is a vector of mathematical variables, and w ("Parameter Vector") is a vector of mathematical parameters of the Model. The Model is designed by choosing a value for the Parameter Vector based on a multiplicity of pairs ("Training Set") $\{x_i, y_i\}$, i=1, ..., P, where $x_i$ and $y_i$ are known corresponding example values for x and y, respectively. Let $\hat{y}_i$ denote the value produced by substitution of $x_i$ for x in the Model. The Parameter Vector is chosen via a mathematical optimization procedure such that, in general, a value $\hat{y}_i$ ("Predicted Label") closely approximates the corresponding value $y_i$ ("True Label"). The Model is said to predict the Label based on the Input. A vector that represents the Input or Label can describe an image if its elements are the pixel values of an image arranged in lexicographic order. A vector that represents the Input or Label can alternatively describe a multiplicity of images by concatenation of vectors representing the individual images to form the vector.

Certain Definitions

Unless otherwise defined, all technical terms used herein have the same meaning as commonly understood by one of ordinary skill in the art to which the present subject matter belongs. As used in this specification and the appended claims, the singular forms "a," "an," and "the" include plural references unless the context clearly dictates otherwise. Any reference to "or" herein is intended to encompass "and/or" unless otherwise stated.

As used herein, a "High-Quality Image" is a frame of an ultrasound image sequence in which the data acquisition parameters have been chosen in such a way as to produce acceptably high image quality in a manner that would be feasible in actual operation of the device in its intended application.

As used herein, a "Reduced-Quality Image" is a frame of an ultrasound image sequence in which, at the expense of reduced image quality, the data acquisition parameters have been deliberately chosen to reduce power consumption, size or cost of the device relative to that required to obtain a High-Quality Image.

As used herein, a "Restored Image" is a frame of an ultrasound image sequence obtained by applying a Model to one or more Reduced-Quality Images to counteract the loss of image quality in the Reduced-Quality Images, thereby restoring image quality to approximate that of a High-Quality Image. A Restored Image comprises a Predicted Label produced by the Model.

As used herein, an "Enhanced-Quality Image" is a frame of an ultrasound image sequence, created solely for purposes of training the Model, which is obtained by applying techniques and design parameters that would be infeasible in actual operation of the imaging device in its intended application, including: 1) imaging with a device different from the one that will be used in operation (and which provides superior image quality). Note that this device does not necessarily need to be an ultrasound device, it could be of a different modality: e.g., CT, MRI, OCT, etc.; 2) enhancing High-Quality Images with an algorithm that would involve computational requirements that would be infeasible in actual operation of the device in its intended application; or 3) imaging with scanning parameters or system configuration that would involve excessive power, size, or cost requirements that could not be replicated in actual operation of the device in its intended application.

Scanning Procedures

We consider two scanning procedures, illustrated in FIG. 1. In Scan Procedure 1, the ultrasound device is programmed to acquire data such that every Nth frame of the acquired ultrasound image sequence is a High-Quality Image, with the rest of the frames being Reduced-Quality Images. We will refer to the every Nth frame as an "Anchor Frame." In Scan Procedure 2, the ultrasound device is programmed so that every frame of the acquired ultrasound image sequence is a Reduced-Quality Image. A wide range of image sizes/qualities are alternatively suitable, depending on what image sizes/qualities the ultrasound device is capable of providing or configures to provide.

Using a Machine Learning Model to Recover Image Quality

The subject matter described herein comprises the acquisition of ultrasound image frames according to Scan Procedure 1 or Scan Procedure 2, followed by application of a Model to predict Restored Images based on the acquired images. Thus, one or more Restored Images comprise the Predicted Label, and one or more acquired images comprise the Input to the Model.

In one embodiment, a Model is designed to restore each Reduced-Quality Image in Scan Procedure 1 by predicting a Restored Image based on a Reduced-Quality Image and the two Anchor Frames that are nearest to it in the sequence (closest in time).

In another embodiment, a Model is designed to restore each Reduced-Quality Image by predicting a Restored Image based on frames from farther in the past (not closest in time). In such embodiments, the past frames optionally include: one or more previous high-quality frames, one or more previous Reduced-Quality frames, and even one or more frames produced earlier in the sequence by the processing methods described herein, and combinations thereof.

Figure 2A:
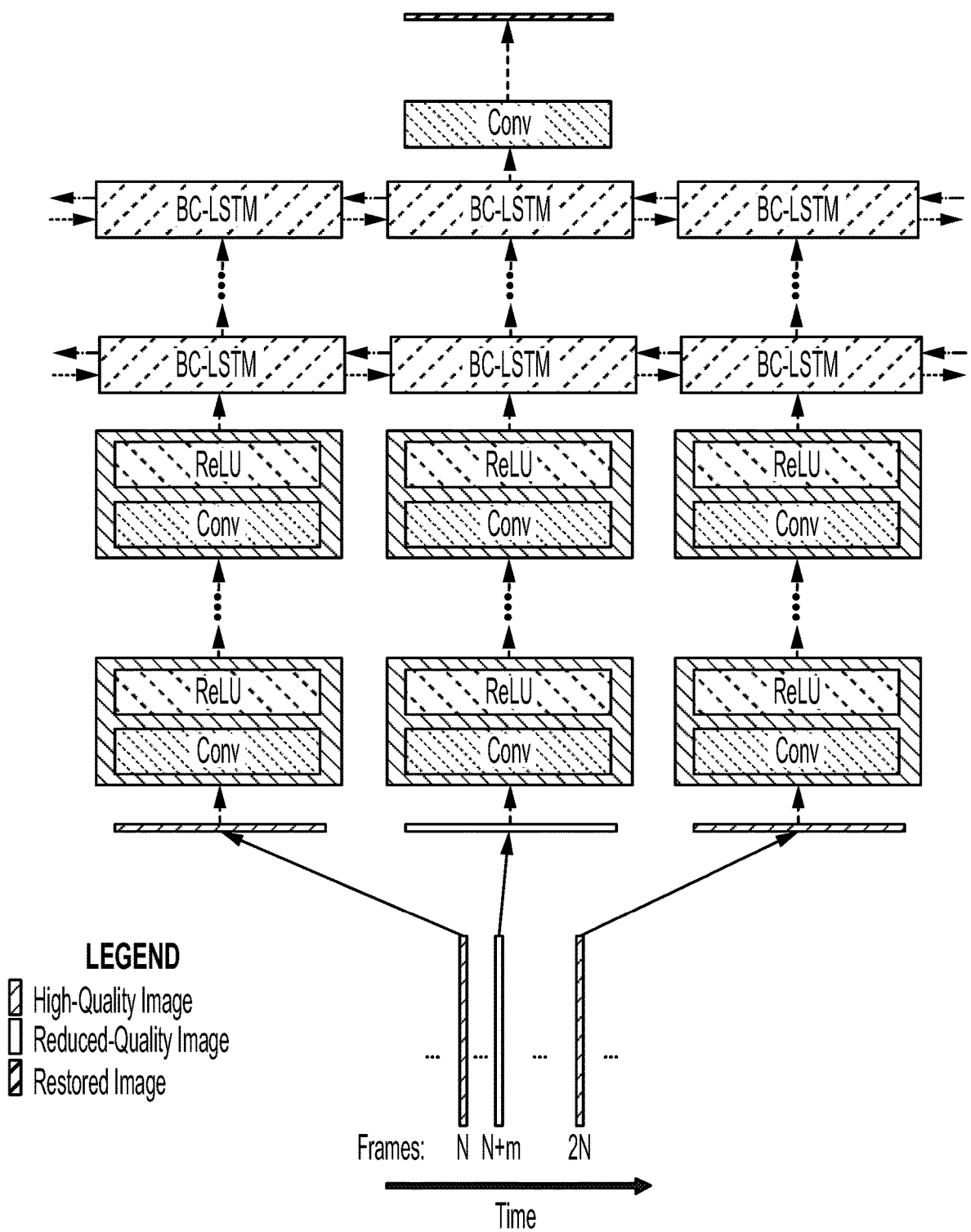
FIG. 2A illustrates a spatio-temporal prediction Model comprising Cony and BC-LSTM modules (ReLU indicates a rectified linear unit)

An exemplary Model to predict a Restored Image can be constructed using the deep learning architecture shown in FIG. 2A (with detail provided in FIG. 2B), comprising convolutional neural network (Cony) layers and bidirectional, convolutional, long short-term memory (BC-LSTM) layers. In this embodiment, the purpose of the Cony and ReLU layers is to capture and analyze spatial features of the image frames. The initial Cony layers have the effect of determining spatial features of the image. The BC-LSTM layers use information from the two Anchor Frames to assist in restoring the Reduced-Quality Image. In this embodiment, the BC-LSTM exploits temporal relationships among the image frames. The final Cony layer (uppermost in FIG. 2A) aggregates the outputs of the BC-LSTM modules to form the Restored Image.

Figure 2B:
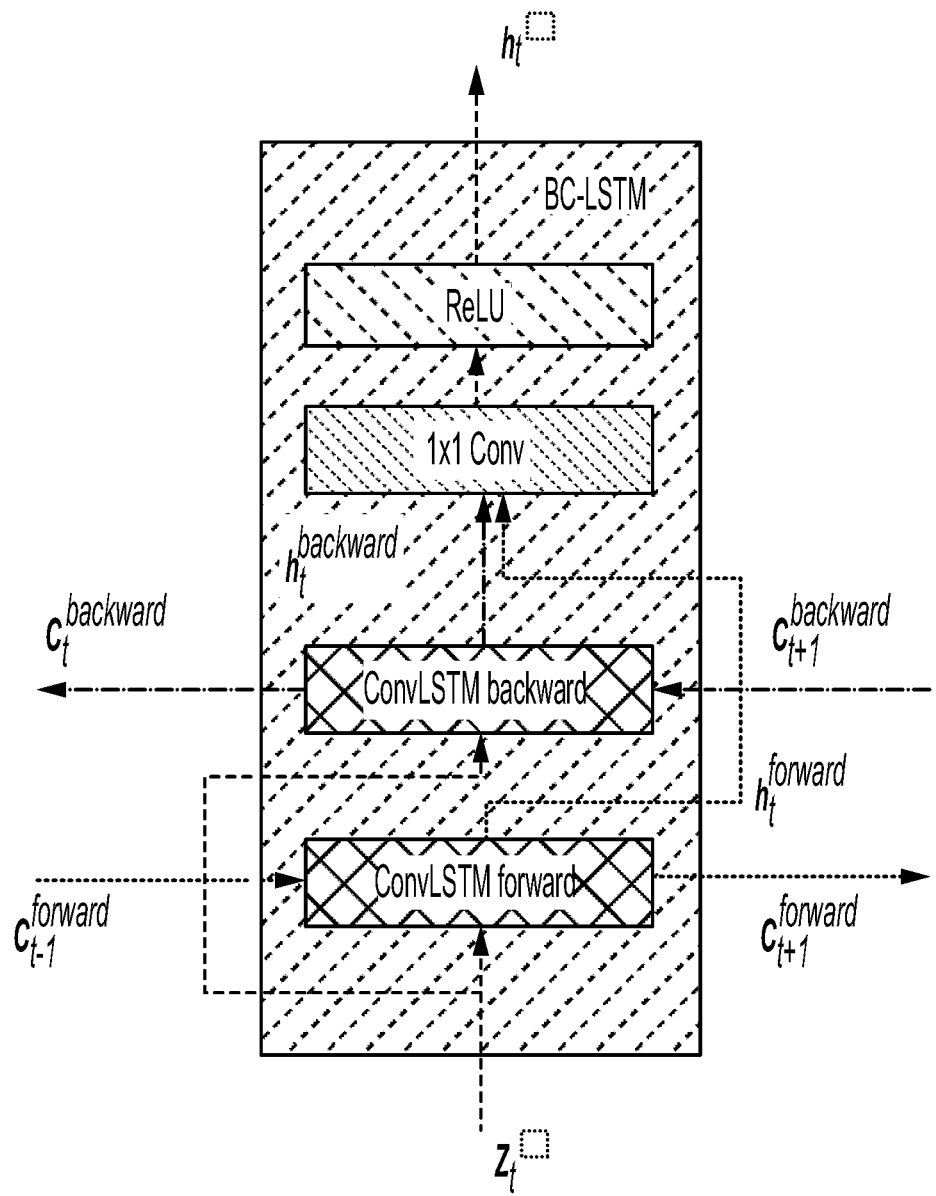
FIG. 2B illustrates the internal structure of a BC-LSTM module of FIG. 2A.

In FIG. 2B, the "ConvLSTM backward" modules within all the "BC-LSTM modules" share the same parameters, whereas the Cony layers do not necessarily share common parameter values.

In this embodiment, training of the Model is accomplished by using two Anchor Frames and one Reduced-Quality Image to form the Input (as seen in FIG. 2A), with the True Label being a High-Quality Image or Enhanced-Quality Image depicting the same image content as the Reduced-Quality Image that the Model seeks to restore. In operation, the Model produces a Predicted Label comprising the Restored Image.

In a variation of this embodiment, the Model uses a Reduced-Quality Image and only the most recently acquired Anchor Frame to form the Input, with the Predicted Label comprising a Restored Image. This approach has the benefit of reliance on causal processing (i.e., it does not utilize images acquired after the Reduced-Quality Image), and thus avoids latency (delay) in producing the images. However, this approach has the disadvantage that it only exploits one Anchor Frame.

In a further variation of this embodiment, the Model uses all the acquired images in a sliding time window of length M to form the Input, with the Output comprising Restored Images corresponding to all the acquired images in the time window. If M=N, then every time window of acquired images contains one Anchor Frame and N−1 Reduced-Quality Images. In this instance, it may be beneficial to introduce an input variable to the Model to identify which of the acquired images is the Anchor Frame.

In a further variation of this embodiment, the Model uses unidirectional temporal processing, such as unidirectional convolutional LSTM, working only in the forward time direction.

In a further variation of this embodiment, the Model processes one image at a time, either continuously updating itself based on past information, or processing each image independently.

In a further variation of this embodiment, Scan Procedure 2 is used to acquire the data. In this case, the Model is trained by using one or more Reduced-Quality Images to construct the Inputs, and one or more corresponding High-Quality Images or Enhanced-Quality Images to construct the True Labels.

In each of these embodiments, the temporal processing provided by LSTM can be replaced by a convolutional neural network. This network can exhibit long-term memory of the image content seen in the image sequence if the temporal convolutions included in the model are dilated convolutions. Alternatively, the spatial and temporal processing can be merged within a unified spatio-temporal convolutional neural network architecture.

In each of these embodiments, the Model can be trained to predict either a High-Quality Image or an Enhanced-Quality Image by appropriate construction of the Training Set.

In each of these embodiments, the Model can be used to improve the quality of the Anchor Frames by using Enhanced-Quality Images as the Labels in the Training Set.

An alternative to the embodiment illustrated in FIG. 2A, still within the scope of the subject matter provided herein, is based on three-dimensional convolutional neural network layers (e.g., no BC-LSTM), with two of these three dimensions being spatial coordinates, and the third dimension being the time coordinate. In this alternative embodiment, the temporal nature of the image sequence is captured by this third dimension.

Power Saving Methods that Impact Image Quality

Reduction in Receive Channel Count

In some embodiments, the front-end system hardware can perform analog signal conditioning, digitization, demodulation, decimation, beamforming, etc. One way of reducing the power consumed by the front-end hardware is to reduce the number of receive channels that are being processed. This manifests itself as a loss of spatial resolution, contrast resolution, and signal-to-noise ratio (SNR). In one case where a smaller aperture is used on receive (64 elements vs. 128 elements) the spatial resolution is decreased by a factor of 2 in the azimuthal dimension. In another embodiment, the number of receive elements is reduced by using the even or odd elements. This method maintains azimuthal spatial resolution (same effective aperture size), but sidelobes and grating lobes induced by the poorer spatial sampling decrease the contrast resolution of the resulting image.

It is also worth mentioning that in systems where fixed element pitch results in a steering limitations at higher frequencies due to grating lobes and other spatial sampling artifacts that such an approach could be used to regain image quality. In such an embodiment, one could synthesize virtual elements to achieve a higher spatial sampling rate at the expense of increased computation and power for the "high quality" frame and then use the normal aperture for the low quality frames.

Reduction in Temporal Sampling Frequency

Reducing the temporal sampling frequency of the front-end ADC also reduces power. In an extreme case, reducing the sampling frequency causes temporal aliasing of the ultrasound signal and reduces image contrast and resolution.

Reduction in Phase/Delay Quantization During Beamforming

Reducing the computational complexity of the beamforming process such as reducing the group delay quantization levels or not performing the fine phase alignment reduces processing power. However, this imperfect focusing scheme reduces image quality by deteriorating the point spread function (spatial resolution and contrast resolution).

Reduction in the Number of Transmissions

In this method to reduce power, the number of transmissions is reduced by increasing the transmit line spacing and/or increasing transmit f/ #by restricting the transmit aperture. The overall effect is reducing the number of transmissions and hence receiving processing lines that need to be computed per frame. The effect of this approach is a reduction in image SNR, spatial resolution and image contrast.

Another effect of reducing the number of transmissions would be to increase the number of parallel receive beams processed per transmission. However, forming more receive beams per transmission results in multibeam, block artifacts that are undesirable in terms of image quality. The approaches outlined in this disclosure could be used to address these undesirable imaging artifacts.

Included in this method would be cases where multiple focused transmissions (different transmit focal depths) or retrospective transmit/receive aperture synthesis would be used in order to create a high quality image frame.

Reduction in Transmitted Power

Transmitting at a reduced transmit power (voltage level, number of transmit cycles, weaker focus/plane waves/diverging waves) decreases the SNR. In this case the "high quality" frames would be transmitted at higher voltage levels, perhaps using coded excitation, and/or pulse width modulation, which would have the added benefit of reducing pulse ringdown.

Reduction in Image Processing Complexity

In one embodiment, the Reduced-Quality Image frames are not processed the same way as the High-Quality Image frames in terms of the complexity of the image processing algorithms that are applied (e.g., phase aberration correction, adaptive imaging, aperture coherence function-based imaging techniques, speckle reduction, edge enhancement, etc.). This naturally reduces the spatial resolution, contrast resolution, and potentially SNR in the output image.

While preferred embodiments of the present subject matter have been shown and described herein, it will be obvious to those skilled in the art that such embodiments are provided by way of example only. Numerous variations, changes, and substitutions will now occur to those skilled in the art without departing from the described methods and devices. It should be understood that various alternatives to the embodiments of the subject matter described herein may be employed in practicing the described methods and systems.

The invention claimed is:

1. A medical ultrasound imaging method comprising:
   a) forming a frame of an ultrasound image sequence with high image quality;
   b) forming a frame of the ultrasound image sequence with reduced image quality;
   c) improving the quality of the frame of the ultrasound image sequence with reduced image quality by applying a machine learning model designed to restore a frame of the ultrasound image sequence with reduced image quality by predicting a restored image based on a frame of the ultrasound image sequence with reduced image quality and two anchor frames that are closest in time to the frame of the ultrasound image sequence with reduced image quality, the two anchor frames being of high image quality; and
   d) repeating steps a) through c) until the medical ultrasound imaging is completed;
   wherein the frames are formed using a transducer.

2. The method of claim 1, further comprising improving the quality of the frame of the ultrasound image sequence with high image quality.

3. The method of claim 1, wherein image quality comprises spatial resolution.

4. The method of claim 1, wherein image quality comprises contrast resolution.

5. The method of claim 1, wherein image quality comprises signal-to-noise ratio.

6. The method of claim 1, wherein image quality comprises signal dynamic range.

7. The method of claim 1, wherein each frame is a 2-dimensional image.

8. The method of claim 1, wherein each frame is a 3-dimensional image.

9. The method of claim 1, wherein each frame is a B-Mode image.

10. The method of claim 1, wherein each frame is a color Doppler image.

11. The method of claim 1, wherein each frame is a spectral Doppler strip.

12. The method of claim 1, wherein the reduced image quality is a result of low spatial sampling incurred by using a reduced number of transducer elements, low temporal sampling incurred by using a low temporal sampling rate, low spatial frequency sampling, temporal delay quantization used during a beamforming process, not performing phase aberration correction, not performing aperture coherence function-based imaging techniques, or is due to sending a reduced number of transmissions, increasing line spacing, reducing ensemble length, or a combination thereof.

13. The method of claim 1, wherein the reduced image quality is due to a combination of two or more techniques used to reduce image quality selected from the list consisting of: low spatial sampling incurred by using a reduced number of elements of the transducer, low temporal sampling incurred by using a low temporal sampling rate, low spatial frequency sampling, temporal delay quantization used during a beamforming process, not performing phase aberration correction, not performing aperture coherence function-based imaging techniques, sending a reduced number of transmissions, increasing line spacing, and reducing ensemble length.

14. The method of claim 1, wherein the transducer comprises a pMUT device.

15. The method of claim 1, wherein the frame with high image quality is formed independent of transducer motion.

16. The method of claim 1, wherein the transducer comprises a 1.25D array of elements.

17. The method of claim 1, wherein the transducer comprises a 1.5D array of elements.

18. The method of claim 1, wherein the transducer comprises a 1.75D array of elements.

19. The method of claim 1, wherein the transducer comprises a 2D array of elements.

20. A medical ultrasound imaging system comprising:
   i) a medical ultrasound imaging device comprising an ultrasound transducer; and
   ii) at least one processor;
the system configured to perform functions comprising:
   a) forming, using the ultrasound transducer, a frame of an ultrasound image sequence with high image quality;
   b) forming, using the ultrasound transducer, a frame of the ultrasound image sequence with reduced image quality; and
   c) improving, using the at least one processor, the quality of the frame of the ultrasound image sequence with reduced image quality by applying a machine learning model designed to restore a frame of the ultrasound image sequence with reduced image quality by predicting a restored image based on a frame of the ultrasound image sequence with reduced image quality and two anchor frames that are closest in time to the frame of the ultrasound image sequence with reduced image quality, the two anchor frames being of high image quality.

21. The medical ultrasound imaging system of claim 20, further configured to perform functions comprising improving the quality of the frame of the ultrasound image sequence with high image quality.

22. The medical ultrasound imaging system of claim 20, wherein image quality comprises spatial resolution.

23. The medical ultrasound imaging system of claim 20, wherein image quality comprises contrast resolution.

24. The medical ultrasound imaging system of claim 20, wherein image quality comprises signal-to-noise ratio.

25. The medical ultrasound imaging system of claim 20, wherein image quality comprises signal dynamic range.

26. The medical ultrasound imaging system of claim 20, wherein each frame is a 2-dimensional image.

27. The medical ultrasound imaging system of claim 20, wherein each frame is a 3-dimensional image.

28. The medical ultrasound imaging system of claim 20, wherein each frame is a B-Mode image.

29. The medical ultrasound imaging system of claim 20, wherein each frame is a color Doppler image.

30. The medical ultrasound imaging system of claim 20, wherein each frame is a spectral Doppler strip.

31. The medical ultrasound imaging system of claim 20, wherein the reduced image quality is a result of low spatial sampling incurred by using a reduced number of elements of the ultrasound transducer.

32. The medical ultrasound imaging system of claim 20, wherein the reduced image quality is a result of low temporal sampling incurred by using a low temporal sampling rate.

33. The medical ultrasound imaging system of claim 20, wherein the reduced image quality is a result of low spatial frequency sampling.

34. The medical ultrasound imaging system of claim 20, wherein the reduced image quality is a result of temporal delay quantization used during a beamforming process.

35. The medical ultrasound imaging system of claim 20, wherein the reduced image quality is due to not performing phase aberration correction.

36. The medical ultrasound imaging system of claim 20, wherein the reduced image quality is due to not performing aperture coherence function-based imaging techniques.

37. The medical ultrasound imaging system of claim 20, wherein the reduced image quality is due to sending a reduced number of transmissions, increasing line spacing, reducing ensemble length, or a combination thereof.

38. The medical ultrasound imaging system of claim 20, wherein the reduced image quality is due to a combination of two or more techniques used to reduce image quality selected from the list consisting of: low spatial sampling incurred by using a reduced number of elements of the ultrasound transducer, low temporal sampling incurred by using a low temporal sampling rate, low spatial frequency sampling, temporal delay quantization used during a beamforming process, not performing phase aberration correction, not performing aperture coherence function-based imaging techniques, sending a reduced number of transmissions, increasing line spacing, and reducing ensemble length.

39. The medical ultrasound imaging system of claim 20, wherein the ultrasound transducer comprises a pMUT device.

40. The medical ultrasound imaging system of claim 20, wherein the ultrasound transducer comprises a 1.25D, 1.5D, 1.75D, or 2D array of elements.

41. The medical ultrasound imaging system of claim 20, wherein the at least one processor comprises an application-specific integrated circuit (ASIC).

42. The medical ultrasound imaging system of claim 20, wherein the at least one processor comprises a mobile computing device in communication with the medical ultrasound imaging device.

43. The medical ultrasound imaging system of claim 20, wherein the frames with high image quality are formed independent of a motion of the medical ultrasound imaging device.

44. A medical ultrasound imaging method for improving quality of at least one frame of an ultrasound image sequence comprising a plurality of frames, the method comprising
   forming an inferior frame of the ultrasound image sequence, the inferior frame having reduced image quality;
   forming two anchor frames of the ultrasound image sequence that are closest in time to the inferior frame, the two anchor frames having high image quality; and
   forming a restored frame of the ultrasound image sequence by applying a machine learning model that predicts the restored frame based on the inferior frame and two anchor frames.

45. The method of claim 44, wherein every Nth frame of the ultrasound image sequence formed is an anchor frame with high image quality.

46. The method of claim 44, wherein each frame of the plurality of frames of the ultrasound image sequence is generated at a distinct time point.

47. The method of claim 44, wherein the two anchor frames having high image quality are frames of the ultrasound image sequence in which data acquisition parameters have been chosen to produce acceptable image quality in a manner feasible for actual operation of an ultrasound imaging device.

48. The method of claim 44, wherein the inferior frame is a frame of the ultrasound image sequence in which data acquisition parameters have been deliberately chosen to reduce power consumption, size, or cost of an ultrasound imaging device relative to the power consumption, size, or cost required to obtain a high image quality frame.

\* \* \* \* \*